US012191006B2

(12) United States Patent
Miyauchi et al.

(10) Patent No.: US 12,191,006 B2
(45) Date of Patent: * Jan. 7, 2025

(54) PRODUCTION DEVICE, SYSTEM, AND METHOD

(71) Applicant: PharmaBio Corporation, Aichi (JP)

(72) Inventors: Hidemasa Miyauchi, Aichi (JP); Hitoshi Kusano, Aichi (JP)

(73) Assignee: PharmaBio Corporation, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,328

(22) Filed: Jan. 13, 2023

(65) Prior Publication Data

US 2023/0162822 A1 May 25, 2023

Related U.S. Application Data

(63) Continuation of application No. 16/643,305, filed as application No. PCT/JP2018/030656 on Aug. 20, 2018, now Pat. No. 11,574,709.

(30) Foreign Application Priority Data

Aug. 30, 2017 (JP) .................................. 2017-165283

(51) Int. Cl.
*G16H 10/40* (2018.01)
*A61K 35/14* (2015.01)
(Continued)

(52) U.S. Cl.
CPC ............ *G16H 10/40* (2018.01); *A61K 35/14* (2013.01); *A61K 35/36* (2013.01); *A61K 35/38* (2013.01);
(Continued)

(58) Field of Classification Search
CPC ....... G16H 10/40; G16H 40/67; C12M 21/00; C12M 21/08; C12M 41/30; C12M 41/36
See application file for complete search history.

(56) References Cited

U.S. PATENT DOCUMENTS

| 9,069,345 B2 | 6/2015 | McCready et al. |
| 2005/0102320 A1 * | 5/2005 | Breimesser ...... G05B 19/41865 |

(Continued)

FOREIGN PATENT DOCUMENTS

| JP | 2012-515984 A | 7/2012 |
| JP | 2015-100309 A | 6/2015 |

(Continued)

OTHER PUBLICATIONS

Abstracts from the Aerosol Society Drug Delivery to the Lungs; Journal of Aerosol Medicine and Pulmonary Drug Delivery26.4: A1-A27. Mary Ann Liebert, Inc. (Aug. 2013) (Year: 2013).*

(Continued)

*Primary Examiner* — Hiep V Nguyen
(74) *Attorney, Agent, or Firm* — Knobbe, Martens, Olson & Bear, LLP

(57) ABSTRACT

Production of "regenerative medicine products" is facilitated using a quality by design (QbD) approach. A production device produces a medical product and analyzes a starting material and a central management device determines processing conditions in the production device. By transmitting and receiving data pertaining to the starting material between the production device and central management device data, the medical product is produced while production conditions therefor are continuously optimized. Thus, it is easy to produce a medical product while reducing or eliminating effects from changes in cells and tissues over time, from oscillation during transport, and from changes in surrounding environment such as changes in temperature, (Continued)

and to produce the desired medical product even when there are individual differences in the starting material.

12 Claims, 9 Drawing Sheets

(51) Int. Cl.
    *A61K 35/36*     (2015.01)
    *A61K 35/38*     (2015.01)
    *A61L 27/38*     (2006.01)
    *C12M 1/34*     (2006.01)
    *C12M 3/00*     (2006.01)
    *G16H 40/67*     (2018.01)

(52) U.S. Cl.
CPC ............. *A61L 27/38* (2013.01); *C12M 21/08* (2013.01); *C12M 41/36* (2013.01); *G16H 40/67* (2018.01)

(56) References Cited

U.S. PATENT DOCUMENTS

| | | | |
|---|---|---|---|
| 2010/0191361 A1 | 7/2010 | McCready et al. | |
| 2010/0256816 A1 | 10/2010 | Popp | |
| 2012/0148540 A1* | 6/2012 | Freeman | A61P 5/06 |
| | | | 435/375 |
| 2016/0264922 A1 | 9/2016 | Ozaki et al. | |

FOREIGN PATENT DOCUMENTS

| | | | |
|---|---|---|---|
| WO | WO-2011106792 A2 * | 9/2011 | ........... A61B 5/0059 |
| WO | WO 2015/181966 A1 | 12/2015 | |

OTHER PUBLICATIONS

Costa, Pedro Ferreira da; Development of advanced cell/tissue culture systems, based on enhanced polymeric scaffolds and sophisticated bioreactors, for tissue engineering applications; Universidade do Minho (Portugal). ProQuest Dissertations Publishing, 2013. 10592737 (Year: 2013).*

"Abstracts from the Aerosol Society Drug Delivery to the Lungs 22", Journal of Aerosol Medicine and Pulmonary Drug Delivery, 26(4): A1-A27, 2013.

Branke et al., "Industry 4.0—A vision also for personalized medicine supply chains?", Cell and Gene Therapy Insights, Jul. 5, 2016, vol. 2, pp. 263-270.

Extended European Search Report issued in European Application No. 18850070.6, dated May 7, 2021.

Harrison et al., "Automating decentralized manufacturing of cell & gene therapy products", Cell and Gene Therapy Insights, Nov. 10, 2016, vol. 2, No. 1, pp. 489-497.

Kawasaki, Nana et al., "Research on each description of medicines such as antibody pharmaceuticals produced and controlled by quality by design" Pharmaceutical and Medical Device Regulatory Science Society of Japan, vol. 47, No. 1 (2016) p. 60-63 and 81.

Lipsitz, et al., "Quality cell therapy manufacturing by design", Nature Biotechnology, 2016, vol. 34, No. 4, pp. 393-400, abstract, p. 396, left column lines 12-22, fig. 2.

Marasco, DM et al., "Development and Characterization of a Cell Culture Manufacturing Process Using Quality by Design(QbD) Principles", Advances in Biochemical Engineering/Biotechnology, 2014, vol. 139, pp. 93-121.

Sequin, L.R., *Variables Influencing Growth and Morphology of Colonies of Cells Derived from Human Amniotic Fluid*, ProQuest Dissertations Publishing, in 251 pages, 1980.

International Search Report issued in application No. PCT/JP2018/030656, dated Jan. 8, 2019.

Office Action issued in Japanese Application No. 2019-539371, dated Sep. 26, 2023.

Mano, E., "Quality by Design Introduction What is QbD from the regulatory perspective of pharmaceutical companies?" Pharmacia, 2017, 53(5): 415-419.

Office Action issued in Japanese Application No. 2019-539371, dated Mar. 14, 2023.

* cited by examiner

PRODUCTION DEVICE, SYSTEM, AND METHOD

TECHNICAL FIELD

The present invention relates to a production device, a system, and a method. For example, one embodiment of the present invention relates to a production device, a system, and a method for producing a product that is used for processing human or animal cells or tissues, for reconstructing, repairing, or forming a structure or a function of a body, or for treating or preventing diseases.

BACKGROUND ART

In Japan, it is often necessary to conduct mass and long-term non-clinical and clinical trials (clinical trials) in order to receive pharmaceuticals approval. Therefore, even when an effective pharmaceuticals is invented, patients often have to wait for approval.

In 2014, Japanese Pharmaceutical Affairs Law was revised. As a result of the revision, a new category of "regenerative medicine products" was established in the Pharmaceutical Affairs Law. For "regenerative medicine products" newly introduced, if safety is confirmed and efficacy is estimated, a conditional approval system that can be approved early has been introduced. As a result, it is highly likely to provide new therapeutic agents for various diseases at an early stage.

Among the "regenerative medicine products", products using microorganism-derived cells or tissues as starting materials are largely classified into "autologous products" and "allogeneic products". The "autologous products" are those that are produced by processing the starting material collected from a patient and used by the same patient. The "allogeneic products" are those that are produced by processing a starting material collected from a healthy person (different from a patient) and are used by the patient. There are individual differences in cells or tissues, and performance and quality of the cells or tissues can change over time, change due to external forces such as oscillation accompanying during transport, or change from changes in surrounding environment. Therefore, it is impossible or extremely difficult to prepare a large amount of starting material with uniform performance and quality. In addition, when the starting material is not uniform, it is difficult to set appropriate production conditions. Thus, when a process (for example, cell cultivation) that showed good results at the research stage (small or proprietary production) is diverted to a commercial stage (mass or general-purpose production), similarly, good results are not always shown. In the worst case, the performance and quality of the cells or tissues may deviate during the process, and thus there is a possibility that the "regenerative medicine products" cannot be produced.

In order to establish a production process of the "regenerative medicine products", there has been proposed a quality-by-design (QbD) approach (see Non Patent Literature 1). The QbD approach is a pharmaceuticals quality management approach based on scientific knowledge and risk management (see operation guideline Q8 (formulation development), Q9 (quality risk management), and Q10 (pharmaceuticals quality system) for maintaining safety and quality defined in International Council for Harmonisation of Technical Requirements for Pharmaceuticals for Human Use:ICH).

In short, in the QbD approach, the production process is systematically managed in the following order.

(I) Set quality target product profile (QTPP) of a final product and critical quality attribute (CQA) of the final product that has a strong influence on the QTPP.

(II) Specify critical process parameter (CPP) that affect the performance and quality of the final product based on risk assessment and multivariate experiment.

(III) Define the range (hereinafter, referred to as "design space") of the CQA and the CPP required to secure QTPP.

In this specification, the QTPP is a product design standard. That is, the QTPP means a summary of the expected quality characteristics of formulation that should be achieved to ensure the required quality when considering the safety and effectiveness of the formulation. In addition, the CQA means physical, chemical, biological, microbiological characteristics or properties that should be within appropriate limits, ranges, and distributions to ensure the required product quality. In addition, the CPP means parameters whose variations affect the CQA and therefore parameters that should be monitored or managed to ensure that the quality required in the process is obtained, among the process parameters.

CITATION LIST

Non Patent Literature

Non Patent Literature 1: Yonatan Y Lipsitz and 2 other authors, "Quality cell therapy manufacturing by design", nature biotechnology, April 2016, Volume 34, Issue 4, p. 393-400

SUMMARY OF INVENTION

Technical Problem

As described above, it is impossible or extremely difficult to prepare a large amount of starting materials (cells or tissues) with uniform performance and quality, and as a result, it is not easy to apply a QbD approach to "regenerative medicine products". Thus, one embodiment of the present invention is to facilitate production of "regenerative medicine products" using a QbD approach.

Solution to Problem

In one embodiment of the present invention, a production device that performs production of a medical product, analyzes a starting material, and the like, and a central management device that determines processing conditions in the production device are provided separately. In addition, the medical product is produced by transmitting and receiving data and the like pertaining to the starting material between the production device and central management device data.

For example, according to one embodiment of the present invention, a production device includes an analysis unit that generates initial analysis data of human or animal cell or tissue that is a starting material of a medical product, a communication unit that transmits the initial analysis data to a central management device and receives initial processing data indicating the processing condition of the starting material optimized by the central management device based on the initial analysis data within a range of a predetermined design space as the processing condition of the starting material, and a processing unit that processes the starting material according to the initial processing data.

According to another embodiment of the present invention, a method for producing a medical product in a production device controlled by a central management device includes generating, by the production device, initial analysis data of human or animal cell that is a starting material of the medical product, transmitting, by the production device, the initial analysis data to the central management device, generating, by the central management device, initial processing data indicating a processing condition of the starting material optimized based on the initial analysis data within a range of a predetermined design space as a processing condition of the starting material, transmitting, by the central management device, the initial processing data to the production device, and processing, by the production device, the starting material according to the initial processing data.

Advantageous Effects of Invention

In one embodiment of the present invention, the production device that performs the production of the medical product, analyzes the starting material, and the like, and the central management device that determines the processing conditions in the production device are provided separately. Thereby, it becomes possible to produce the medical product (on-site production) at the place where the cells or tissues which are the starting materials are collected. As a result, it is easy to produce the medical product while reducing or eliminating effects from changes in cells and tissues over time, from oscillation during transport, and from changes in surrounding environment such as changes in temperature. In addition, the medical product can also be produced near the patient using the medical product. As a result, it is easy to provide the medical product to the patient while reducing or eliminating effects from the change in the cells and tissues constituting the medical product over time, from the oscillation during transport, and from the change in the surrounding environment such as the change in temperature.

In addition, in the embodiment of the present invention, the medical product is produced by transmitting and receiving the data and the like pertaining to the starting material between the production device and the central management device data. Thereby, it possible to determine the processing conditions of the starting material based on the performance and quality of the starting material itself. As a result, even when there are individual differences in the starting material, it becomes easy to produce the desired medical product.

DETAILED DESCRIPTION OF THE PREFERRED EMBODIMENTS

1. Configuration of System

Figure 1:
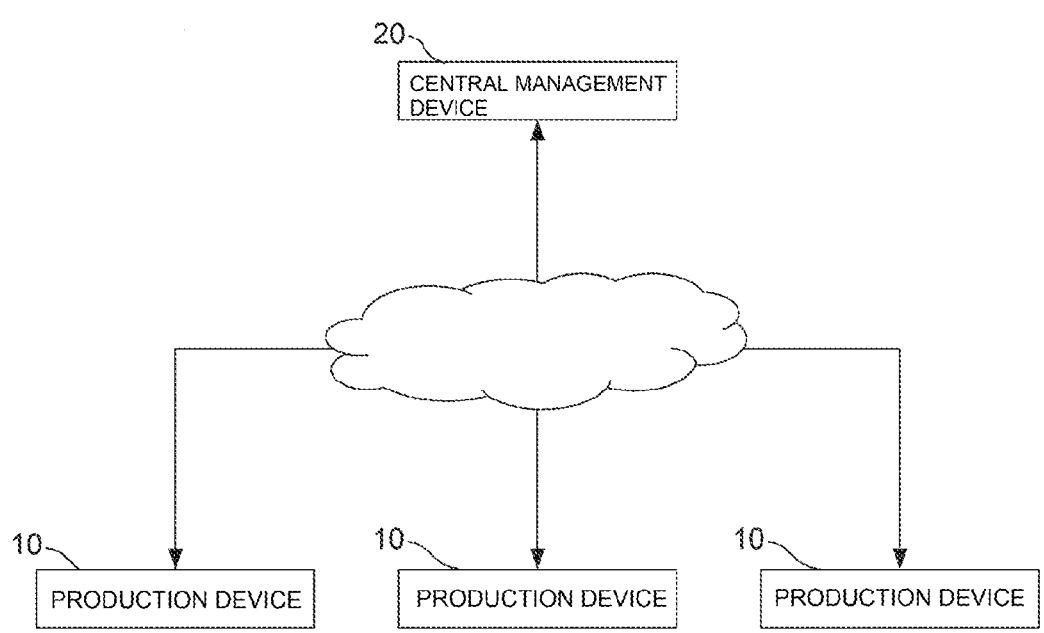
FIG. 1 is a diagram showing an example of a system according to one embodiment of the present invention.

FIG. 1 is a diagram showing an example of a system according to one embodiment of the present invention. The system shown in FIG. 1 includes a plurality of production devices 10 and a central management device 20 that can communicate with each of the plurality of production devices 10 via a network. Note that the network may be constructed by either a wired connection or a wireless connection, or a part thereof may be constructed by the wired connection and the remaining part thereof may be constructed by the wireless connection.

Each of the production device 10 and the central management device 20 shown in FIG. 1 may be installed anywhere as long as the communication is possible via the network. For example, the production device 10 can be installed in a medical institution such as a hospital, a clinic, or a pharmacy, and the central management device 20 can be installed in a corporate head office or the like.

(1) Production Device

Figure 2:
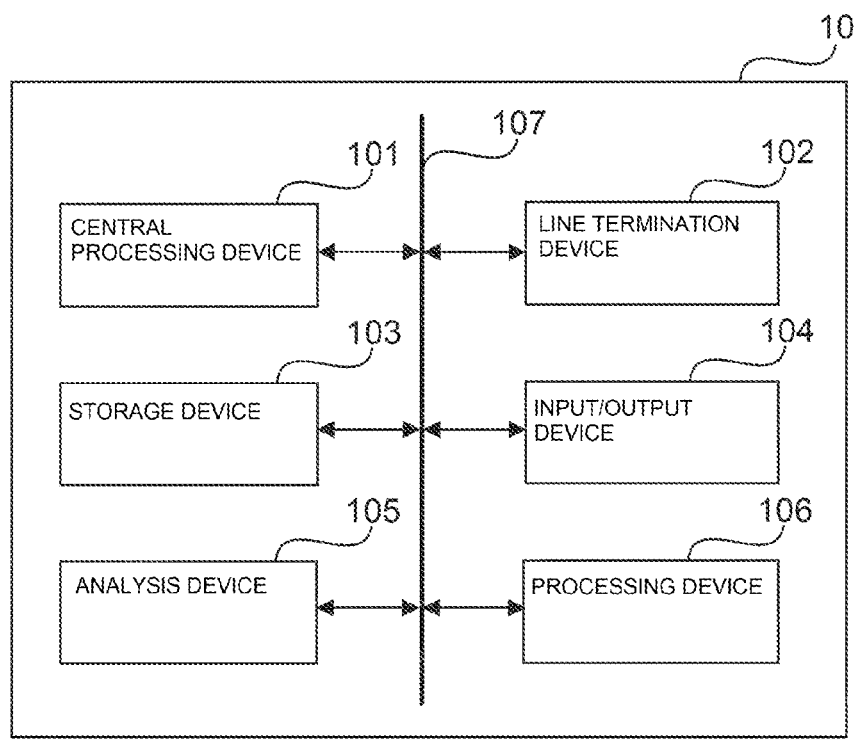
FIG. 2 is a diagram showing an example of components of a production device shown in FIG. 1.

FIG. 2 is a diagram showing an example of components of the production device 10 shown in FIG. 1. The production device 10 shown in FIG. 2 includes a central processing unit (CPU) 101, a line termination device 102, a storage device 103, an input/output device 104, an analysis device 105, and a processing device 106. These components are electrically connected to each other via a bus 107. Note that the production device of one embodiment of the present invention is not limited to those including only the components of the production device 10 shown in FIG. 2. For example, in addition to the components shown in FIG. 2, the production device of one embodiment of the present invention may include a transfer device (for example, robot arm) that transfers a starting material, an intermediate product, or a medical product, which is disposed inside one of the analysis device 105 and the processing device 106, to an inside of the other of the analysis device 105 and the processing device 106.

The central processing unit (CPU) 101 is used to execute an instruction included in software stored in the storage device 103. Specifically, the central processing unit (CPU) 101 is used for generation of a signal including various types of information transmitted to the central management device 20, calculation processing based on an operation (of an input device) of the input/output device 104 by an operator and control (of an output device) of the input/output device 104 for presenting specific information to the operator, analysis of human or animal cells or tissues which are starting materials of a medical product, control of the analysis device 105 for performing analysis of intermediate product obtained by processing the starting materials and/or analysis of the medical product, control of the processing device 106 for processing the starting materials and/or the intermediate product, and the like.

The line termination device 102 is used to transmit various signals generated by the central processing unit (CPU) 101 to the central management device 20, and receive a signal including the processing conditions of the starting material transmitted by the central management device 20 and/or a signal including the processing conditions of the intermediate product. Examples of the line termination device 102 include a modem, an optical line termination device (ONU), and the like.

The storage device 103 is used to store software including instructions executed by the central processing unit 101 and various data generated by the central processing unit 101. Examples of the storage device 103 include a dynamic random access memory (DRAM), a static random access memory (SRAM), a hard disk drive (HDD), and/or a flash memory, a combination thereof, or the like. Further, the storage device 103 may include a volatile storage unit including a DRAM and the like, and a nonvolatile storage unit including an HDD and the like. In this case, for example, the nonvolatile storage unit can be used to store software including instructions to be executed by the central processing unit 101, and the volatile storage unit can be used to temporarily store various data generated by the central processing unit 101.

The input/output device 104 is used for an operator to operate the production device 10 and to present information to the operator. Examples of the input/output device 104 include a touch panel and the like. Further, the input/output device 104 may be separated into an input device and an output device. Examples of the input device include a pointing device such as a touchpad and a mouse, a keyboard, a button, and a microphone, a combination thereof, or the like. In addition, examples of the output device include a display (monitor) and a speaker, or a combination thereof.

The analysis device 105 is used to analyze human or animal cells or tissues which are starting materials of a medical product, an intermediate product and a medical product obtained by processing the starting materials, and body fluids such as blood and saliva, body hair such as hair, nails, and the like that are collected from a human or an animal providing the starting materials. Examples of the analysis device 105 include a freeze drying device, a sample collection device, a blood analysis device, a flow cytometer, a liquid chromatography, a gas chromatography, a mass analysis device, an image analysis device, a cell analysis device, a gene amplification device, a gene analysis device, an enzyme immunoreactor, a spectrophotometer, an absorptiometer, a weigh scale, a thermometer, a densitometer, an osmometer, a pH meter, a photoelectric sensor, a voltmeter, an ammeter, an imaging device, a microbial culture device, a microbial analysis device, a nuclear magnetic resonance device, an X-irradiation device, a computed tomography device, an ultrasonic tomography device, an X-ray imaging device, two or more combinations thereof, and the like.

The processing device 106 is used for processing (for example, culturing) the starting material and the intermediate product. Examples of the processing device 106 include various cell separators that include a freeze drying device, a laser microdissection device, a dispersing device, a crushing device, a centrifugal separation (including elutriation) device, a separation device using adhesion or magnetic bead, a cell sorting device, a gene amplification device, a gene introduction device using methods such as an electroporation method, a lipofection method, a particle gun method, an ultrasonic method, and a virus vector method or using methods not using these methods, a gene modification device using a nuclease, a constant temperature device, a liquid culture medium dialysis device, an adsorption device, a liquid culture medium circulation device, a trace substance addition device, a pressurizing and depressurizing device, a shaking device, an oscillation generation device, an ultrasonic generation device, a magnetic field generation device, a program freezing device, a cell thawing device, a heating device, a cooling device, an aseptic filling device, an aseptic maintenance device, an air conditioner and a radiation irradiation device, two or more combinations thereof, and the like.

Figure 3:
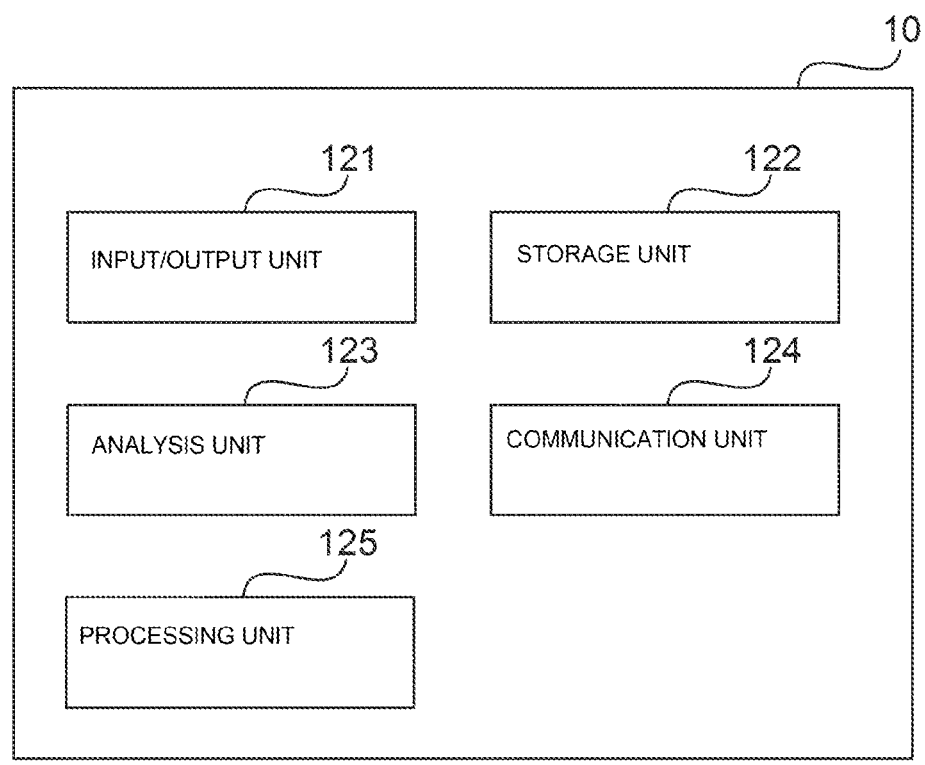
FIG. 3 is a diagram showing an example of functional units of the production device shown in FIG. 1.

FIG. 3 is a diagram showing an example of functional units of the production device 10 shown in FIG. 1. The production device 10 shown in FIG. 3 includes an input/output unit 121, a storage unit 122, an analysis unit 123, a communication unit 124, and a processing unit 125. Note that the production device of one embodiment of the present invention is not limited to those including only the functional units of the production device 10 shown in FIG. 3. For example, as the production device of one embodiment of the present invention, in addition to the functional units shown in FIG. 3, a transfer unit having a function of transferring a starting material, an intermediate product, or a medical product to a desired place (for example, from one of the analysis unit and the processing unit to the other of the analysis unit and the processing unit) may be provided inside the production device 10.

The input/output unit 121 includes a function of receiving instructions and the like pertaining to production of a medical product from the operator, and presenting information pertaining to the production of the medical product to the operator. For example, the input/output unit 121 may include a function of presenting to an operator that a medical product is not currently being produced in the production device 10, presenting an option as to whether or not to start the production of the medical product, and receiving the instruction when the operator selects that the production of the medical product starts. Note that the function of the input/output unit 121 is implemented by the central processing unit 101, the input/output device 104, and the like shown in FIG. 2.

The storage unit 122 has a function of storing data necessary for producing the medical product and updating existing data. For example, the storage unit 122 may include a function of storing analysis data obtained by analyzing the starting material, the intermediate product, and the medical product and processing data indicating processing conditions of the starting material and the intermediate product transmitted from the central management device 20, and updating a signal for changing conditions when these analyses are performed and/or a signal for changing a design space set in a particular production process when the signals are transmitted from the central management device 20. Note that the function of the storage unit 122 is implemented by the central processing unit 101, the storage device 104, and the like shown in FIG. 2.

The analysis unit 123 includes a function of analyzing the starting material, the intermediate product, and the medical product (referred to as "starting material and the like" in this paragraph). For example, the analysis unit 123 may include a function of analyzing at least one of sizes, color tones, weights, cell particle sizes, expression rates of various cell surface antigens, the amount of various gene expressions, the number of viable cells, viable cell rates, and expressed genes of cells or tissues constituting starting materials and the like, and pathogenic microorganisms and proliferating viruses included in the starting material and the like. In addition, the analysis unit 123 may include a function of analyzing at least one of properties, compositions, drug concentrations, and genes of cells or tissues constituting body fluids such as blood and saliva, body hairs such as hair, nails, and the like (referred to as "body fluid and the like" in this paragraph), and proliferating viruses included in the body fluid and the like. Note that the function of the analysis unit 123 is implemented by the central processing unit 101, the analysis device 105, and the like shown in FIG. 2.

The communication unit 124 has a function of transmitting a signal to the central management device 20 and receiving a signal transmitted by the central management device 20. For example, the communication unit 124 may include a function of transmitting a signal indicating the analysis result of the starting material and a signal requesting to teach optimal processing conditions for the signal, and also receiving a signal indicating the processing conditions of the starting material transmitted by the central management device 20. Note that the function of the communication unit 124 is implemented by the central processing unit 101, the line termination device 102, and the like shown in FIG. 2.

The processing unit 125 includes a function of processing the starting material and/or the intermediate product according to the processing conditions transmitted from the central management device 20. For example, the processing unit 125 may include a function of processing human or animal cells or tissues which are starting materials or intermediate products (specifically, dispersion of tissue, crushing, laser microdissection, centrifugation (including elutriation), various cell separation including adhesion or separation using magnetic bead, introduction of genes using methods such as an electroporation method, a lipofection method, a particle gun method, an ultrasonic method, and a virus vector method or using methods not using these methods, modification of genes using various nucleases, cultivation, pressurization/depressurization, shaking, oscillation irradiation, ultrasonic irradiation, magnetic field generation, freezing, thawing, heating, cooling, replacing all or part of media, adjustment of a surface area in a culture vessel, control of a cell concentration by adjusting the amount of medium, control of temperature, illumination, oscillation, current, magnetic field, barometric pressure, and atmosphere, addition of solvents or additives, aseptic filling, and the like), and modifying the ability. Note that the function of the processing unit 125 is implemented by the central processing unit 101, the processing device 106, and the like shown in FIG. 2.

(2) Central Management Device

Figure 4:
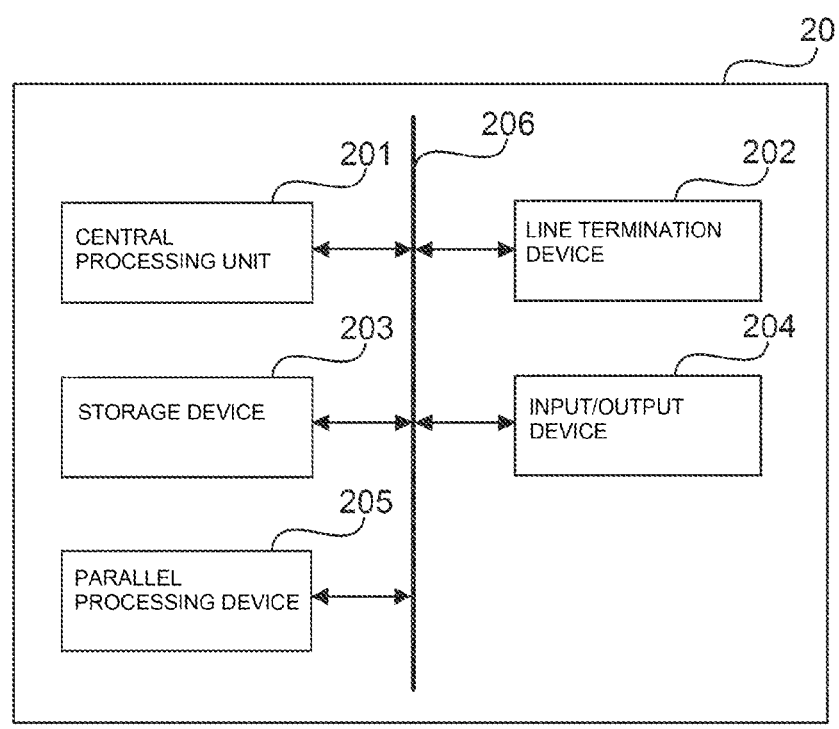
FIG. 4 is a diagram showing an example of components of a central management device shown in FIG. 1.

FIG. 4 is a diagram showing an example of components of the central management device 20 shown in FIG. 1. The central management device 20 shown in FIG. 4 includes a central processing unit (CPU) 201, a line termination device 202, a storage device 203, an input/output device 204, and a parallel processing device 205. These components are electrically connected to each other via a bus 206. Note that the production device of one embodiment of the present invention is not limited to those including only the components of the central management device 20 shown in FIG. 4. For example, in addition to the components shown in FIG. 4, the central management device of one embodiment of the present invention may experimentally include devices similar to the analysis device 105 and the processing device 106 included in the production device 10.

The central processing unit (CPU) 201 is used to execute an instruction (excluding those executed by the parallel processing device 205) included in software stored in the storage device 203. Specifically, the central processing unit (CPU) 201 is used to perform generation of signals (excluding those generated by the parallel processing device 205) including various information transmitted to the production device 10 and calculation processing based on the operation (of the input device) of the input/output device 204 by the operator and control (of the output device) of the input/output device 204 for presenting specific information to the operator.

The line termination device 202 is used to transmit various signals generated by the central processing unit (CPU) 201 and the parallel processing device 205 to the production device 10, and receive a signal indicating an analysis result of the starting material transmitted by the production device 10 and/or a signal indicating an analysis result of the intermediate product. Examples of the line termination device 202 include a modem, an optical line termination device (ONU), and the like.

The storage device 203 is used to store software including instructions executed by the central processing unit 201 and the parallel processing device 205 and various data generated by the central processing unit 201 and the parallel processing device 205. Examples of the storage device 203 include a DRAM, an SRAM, an HDD and/or a flash memory, a combination thereof, or the like. Further, the storage device 203 may include a volatile storage unit including a DRAM and the like, and a nonvolatile storage unit including an HDD and the like. In this case, for example, the nonvolatile storage unit can be used to store software including instructions to be executed by the central processing unit 201, and the volatile storage unit can be used to temporarily store various data generated by the central processing unit 201.

The input/output device 204 is used for an operator to operate the central management device 20 and to present information to the operator. Examples of the input/output device 204 include a touch panel and the like. Further, the input/output device 204 may be separated into an input device and an output device. Examples of the input device include a pointing device such as a touchpad and a mouse, a keyboard, a button, and a microphone, a combination thereof, or the like. In addition, examples of the output device include a display (monitor) and a speaker, or a combination thereof.

The parallel processing device 205 is used to execute an instruction (excluding those executed by the central processing unit 201) included in software stored in the storage device 203. For example, the parallel processing device 205 is used to determine the optimal processing conditions for the starting material or the intermediate product based on the analysis result of the starting material or the intermediate product transmitted from the production device 10 within a predetermined design space, and furthermore, perform machine learning using the analysis results of the starting material, the intermediate product, and the medical product as data.

Figure 5:
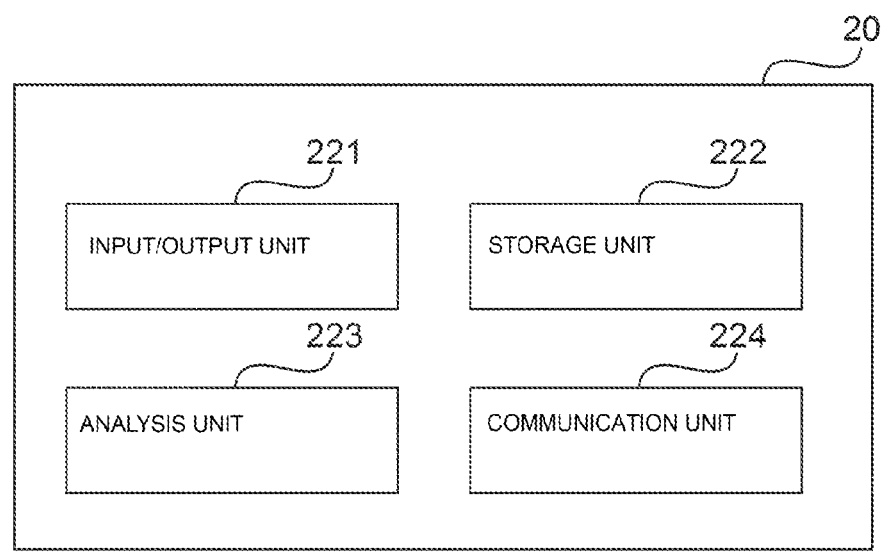
FIG. 5 is a diagram showing an example of functional units of the central management device shown in FIG. 1.

FIG. 5 is a diagram showing an example of functional units of the central management device 20 shown in FIG. 1. The central management device 20 shown in FIG. 5 includes an input/output unit 221, a storage unit 222, an analysis unit 223, and a communication unit 224. Note that the central management device of one embodiment of the present invention is not limited to those including only the functional units of the central management device 20 shown in FIG. 5. For example, the inside of the central management device 20 as the central management device of one embodiment of the present invention may be provided with an analysis unit that includes a function of analyzing samples of the starting material, the intermediate product, or the medical product and a processing unit that includes a function of processing samples of the starting material and the intermediate product, in addition to the functional units shown in FIG. 5.

The input/output unit 221 includes a function of receiving instructions and the like pertaining to production of a medical product from the operator, and presenting information pertaining to the production of the medical product to the operator. For example, the input/output unit 221 may include a function of presenting the operator with an option to change the design space of a specific production process as a result of machine learning by the parallel processing device 205, and furthermore, receiving an instruction to change the design space of the specific production process by the operator. Note that the function of the input/output unit 221 is implemented by the central processing unit 201, the input/output device 204, and the like shown in FIG. 4.

The storage unit 222 includes a function of storing data necessary for producing the medical product and updating existing data. For example, the storage unit 222 may include a function of storing the analysis data of the starting material, the intermediate product, and the medical product transmitted from a plurality of production devices 10 so far and the processing data indicating the processing conditions of the starting material and the intermediate product determined using the parallel processing device 205, and furthermore, updating an instruction for changing the design space of the specific production process when the instruction is received from the operator. Note that the function of the storage unit 222 is implemented by the central processing unit 201, the storage device 204, and the like shown in FIG. 4.

The analysis unit 223 includes a function of deriving the optimal processing conditions for the starting material or the intermediate product. For example, the analysis unit 223 includes a function of determining the processing conditions when the signal indicating the analysis result of the starting material or the intermediate product is transmitted from the production device 10 and furthermore, performing machine learning on the analysis data of the starting material or the intermediate product, the processing data therefor, and the resulting analysis data of the medical product as data. Note that the function of the analysis unit 223 is implemented by the parallel processing device 205 and the like shown in FIG. 4.

The communication unit 224 has a function of transmitting a signal to the production device 10 and receiving a signal transmitted by the production device 10. For example, the communication unit 224 may include a function of transmitting a signal indicating the processing conditions of the starting material and a signal indicating that the starting material is processed accordingly to the production device 10, and furthermore, receiving a signal indicating the analysis result of the starting material transmitted by the production device 10. Note that the function of the communication unit 224 is implemented by the central processing unit 201, the termination device 202, and the like shown in FIG. 2.

2. Sequence of System

FIGS. 6 to 9 are diagrams showing an example of a sequence of a system shown in FIG. 1. Hereinafter, each sequence will be described in detail.

Figure 6:
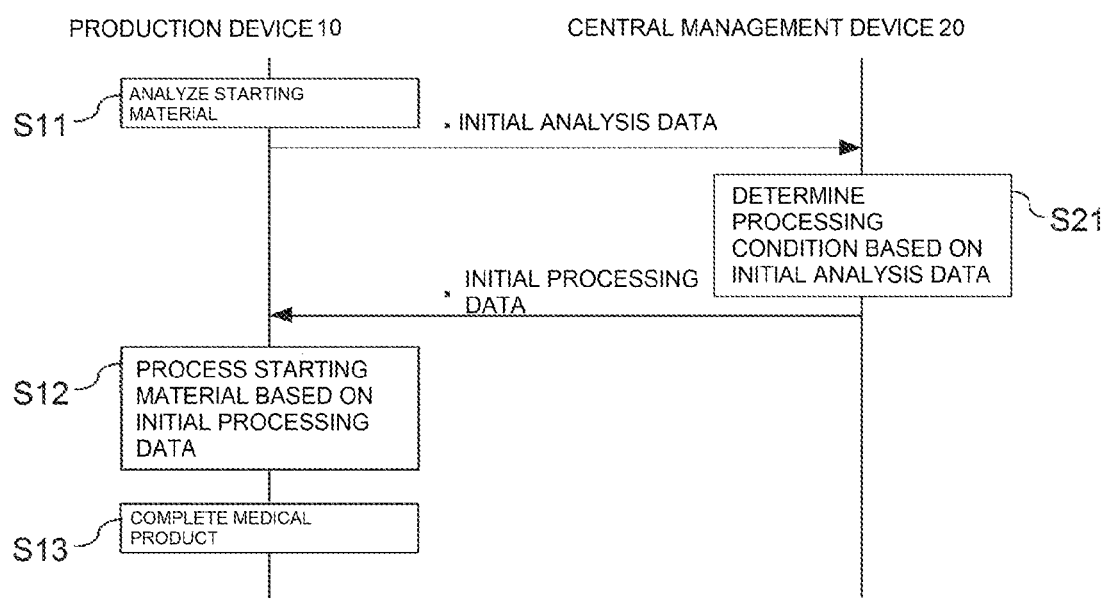
FIG. 6 is a diagram showing an example of a sequence of a system shown in FIG. 1.

(1) As to Sequence Shown in FIG. 6

First, in the production device 10, the analysis of the human or animal cells or tissues, which are the starting materials of the medical product, is performed (S11). Note that examples of the analysis may include measurement of a size, a color tone, a weight, a cell particle size, expression rates of various cell surface antigen, the amount of various gene expression, the number of viable cells, or a viable cell rate of human or animal cell or tissue which is the starting material, and qualitative and quantitative determination of expressed gene or expressed protein, measurement of drug concentration of the starting material, detection and identification of pathogenic microorganisms or proliferating viruses included in the starting material, and the like. The production device 10 transmits the signal (initial analysis data) indicating the analysis result of the starting material to the central management device 20.

Next, in the central management device 20, the processing conditions of the starting material are determined based on the initial analysis data (S21). Note that the processing conditions are determined within the predetermined design space. The central management device 20 transmits the signal (initial processing data) indicating the processing conditions of the starting material to the production device 10.

Next, in the production device 10, the starting material is processed based on the initial processing data (S12). Examples of the processing includes drying, immersion, dispersion, crushing, centrifugation (including elutriation), various cell separations including adhesion or separation using magnetic bead, introduction of gene using methods such as an electroporation method, a lipofection method, a particle gun method, an ultrasonic method, and a virus vector method or methods not using these methods, modification of genes using various nucleases, cultivation, pressurization/depressurization, shaking, oscillation irradiation, ultrasonic irradiation, magnetic field generation, freezing, thawing, heating, cooling, replacing all or part of media, adjustment of a surface area in a culture vessel, control of a cell concentration by adjusting the amount of medium, control of temperature, illumination, oscillation, current, magnetic field, barometric pressure, and atmosphere, addition of solvents or additives, aseptic filling, and the like.

In the sequence shown in FIG. 6, the medical product is completed by the above process (S13).

In the sequence shown in FIG. 6, the separately provided production device 10 and the production device 10 separately provided from the central management device 20 for determining processing conditions produce a medical product. Thereby, the degree of freedom of the production place of the medical product is increased. As a result, it is easy to produce the medical product while reducing or eliminating effects from the change in the human or animal cells and tissues, which are the starting materials, over time, from the oscillation during transport, and from the change in the surrounding environment such as changes in temperature. In addition, the medical product can also be produced near the patient using the medical product. As a result, it is easy to provide the medical product to the patient while reducing or eliminating effects from the change in the cells and tissues constituting the medical product over time, from the oscillation during transport, and from the change in the surrounding environment such as the change in temperature.

In addition, in the sequence shown in FIG. 6, the processing conditions of the starting material are determined based on the analysis result of the starting material. As a result, it is easy to set the optimal processing conditions for the starting material. As a result, even when there are individual differences in the starting material, it becomes easy to produce the desired medical product.

Note that the medical product produced by the sequence shown in FIG. 6 may be either "autologous product" or "allogeneic product". However, when the medical product is the "autologous product", there is a possibility that the quality of cells or tissues (starting materials) collected from a patient may vary greatly depending on the disease state or condition. Even in such a case, in the sequence shown in FIG. 6, since the processing conditions are determined based on the analysis data of the starting material, the medical product can be produced with high accuracy.

Figure 7:
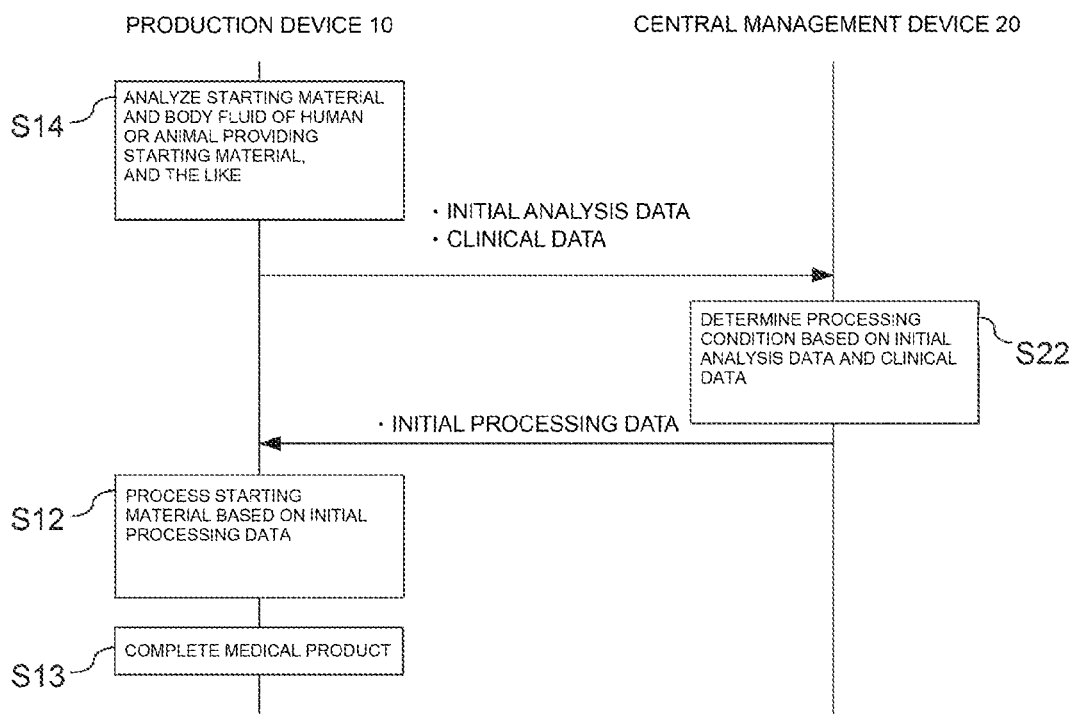
FIG. 7 is a diagram showing an example of the sequence of the system shown in FIG. 1.

(2) As to the Sequence Shown in FIG. 7

First, in the production device 10, not only the analysis (hereinafter referred to as "the former analysis") of the human or animal cells or tissues which are the starting materials of the medical product, but also the analysis (hereinafter, referred to as "the latter analysis") body fluids such as blood and saliva collected from human or animals that have provided the starting material, body hair such as hair, nails, and the like (referred to as "body fluid and the like" in this paragraph) is performed (S14). Examples of the former analysis include at least one of measurement of sizes, color tones, weights, cell particle sizes, expression rates of various cell surface antigens, the amount of various gene expressions, the number of viable cells, or viable cell rates of cells or tissues, analysis of expressed gene, detection and identification of pathogenic microorganisms included in the starting material, and detection and identification of proliferating viruses. In addition, examples of the latter analysis include at least one of analysis of properties, compositions, drug concentration, genes, and the like of cells or tissues, and detection and identification of proliferating viruses included in body fluids, and the like. The production device 10 transmits a signal (initial analysis data) indicating the former analysis result and a signal (clinical data) indicating the latter analysis result to the central management device 20.

Next, in the central management device 20, the processing conditions of the starting material are determined based on the initial analysis data and the clinical data (S22). Note that the processing conditions are determined within the predetermined design space. The central management device 20 transmits the signal (initial processing data) indicating the processing conditions to the production device 10.

Next, in the sequence shown in FIG. 7, the same process as the sequence shown in FIG. 6 is performed (S12), and thus the medical product is completed (S13).

The sequence shown in FIG. 7 has the same advantages as the sequence shown in FIG. 6. In addition, the medical product produced by the sequence shown in FIG. 7 may be either "autologous product" or "allogeneic product". When the medical product is the "autologous product", the sequence shown in FIG. 7 has the above-described advantages.

Further, in the sequence shown in FIG. 7, the processing conditions of the starting material are determined based not only on the analysis result of the starting material, but also on body fluids of human or animals that have provided the starting material, and the like. As a result, it is easy to set the optimal processing conditions for the starting material. As a result, even when there are individual differences in the starting material, it becomes easy to produce the desired medical product.

Figure 8:
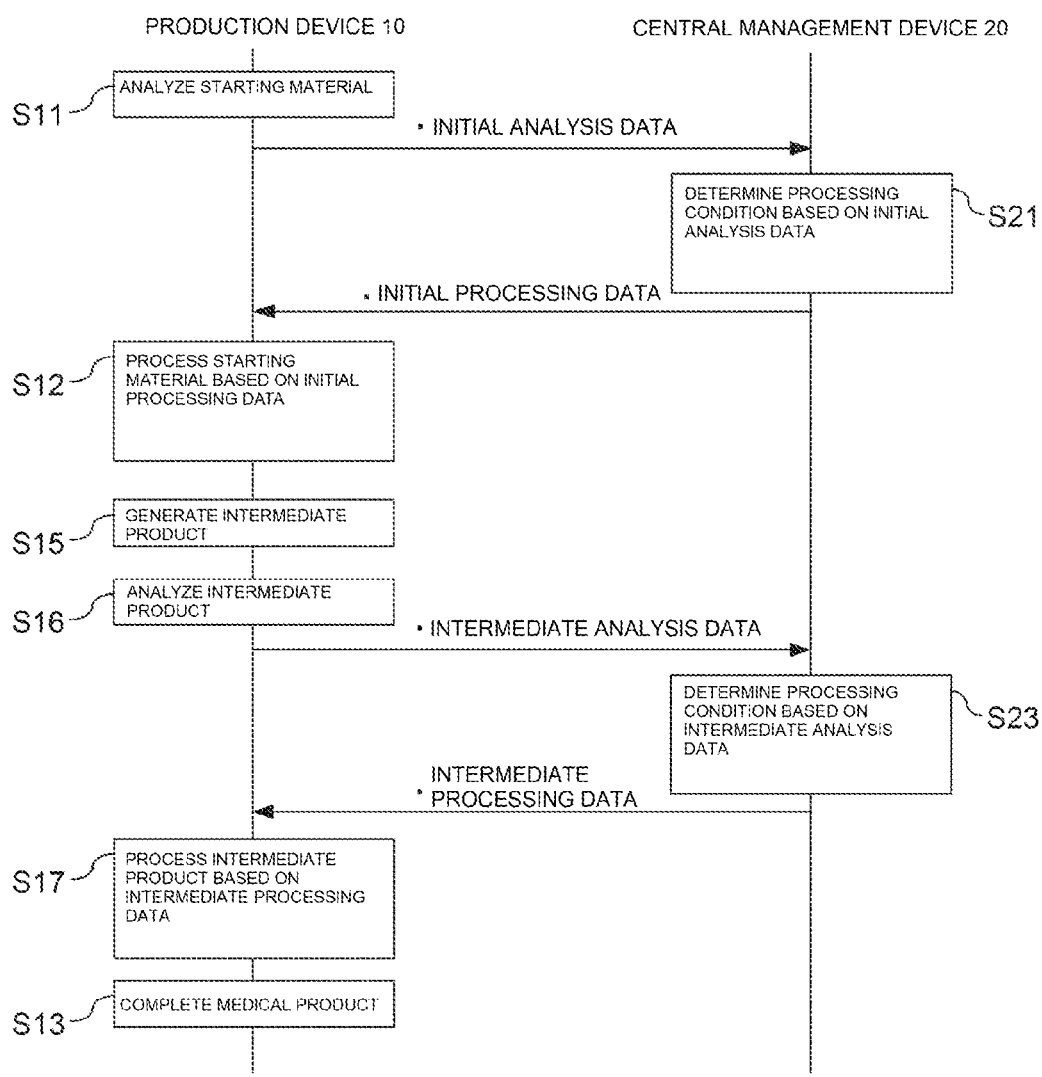
FIG. 8 is a diagram showing an example of the sequence of the system shown in FIG. 1.

(3) As to the Sequence Shown in FIG. 8

First, the same processes as the sequence shown in FIG. 6 are performed (S11, S21, and S12), and thus the intermediate product is generated (S15).

Next, the analysis of the intermediate product is performed (S15). Examples of the analysis include at least one of measurement of the number of viable cells or a viable cell rate in the intermediate product, analysis of cell surface antigens, analysis of various expressed genes, analysis of the amount of various expressed genes, concentration of substances in a culture solution, and detection and identification of pathogenic microorganisms included in the intermediate product, and detection and identification of proliferating viruses, and the like. The production device 10 transmits the signal (initial analysis data) indicating the analysis result of the intermediate product to the central management device 20.

Next, in the central management device 20, the processing conditions of the intermediate product are determined based on the intermediate analysis data (S23). Note that the processing conditions are determined within the predetermined design space. The central management device 20 transmits the signal (intermediate processing data) indicating the processing conditions of the intermediate product to the production device 10.

Next, in the production device 10, the intermediate product is processed based on the initial processing data (S17). Examples of the processing includes drying, immersion, dispersion, crushing, centrifugation (including elutriation), various cell separations including adhesion or separation using magnetic bead, introduction of gene using methods such as an electroporation method, a lipofection method, a particle gun method, an ultrasonic method, and a virus vector method or methods not using these methods, modification of genes using various nucleases, cultivation, pressurization/depressurization, shaking, oscillation irradiation, ultrasonic irradiation, magnetic field generation, freezing, thawing, heating, cooling, replacing all or part of media, adjustment of a surface area in a culture vessel, control of a cell concentration by adjusting the amount of medium, control of temperature, illumination, oscillation, current, magnetic field, barometric pressure, and atmosphere, addition of solvents or additives, aseptic filling, and the like.

In the sequence shown in FIG. 8, the medical product is completed by the above process (S13).

The sequence shown in FIG. 8 has the same advantages as the sequence shown in FIG. 6. In addition, the medical product produced by the sequence shown in FIG. 8 may be either "autologous product" or "allogeneic product". When the medical product is the "autologous product", the sequence shown in FIG. 8 has the above-described advantages.

Further, in the sequence shown in FIG. 8, the production process of the medical product is determined based not only on the analysis result of the starting material but also on the analysis result of the intermediate material. As a result, it possible to set the optimal processing conditions for the intermediate product. As a result, it is possible to reduce the probability that the performance and quality of the intermediate product deviate during the production process.

Figure 9:
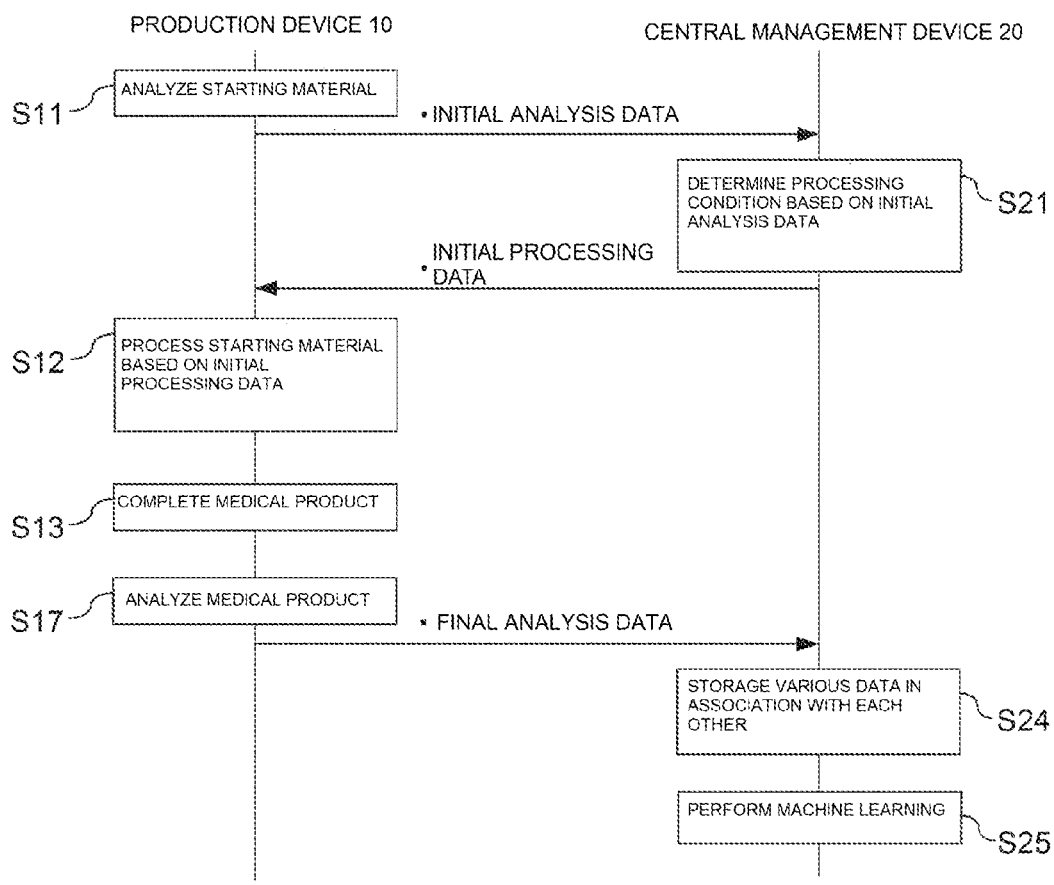
FIG. 9 is a diagram showing an example of the sequence of the system shown in FIG. 1.

(4) As to the Sequence Shown in FIG. 9

First, the same process as the sequence shown in FIG. 6 is performed (S11, S21, and S12), and thus the medical product is completed (S13).

Next, the analysis of the medical product is performed (S17). Example of the analysis includes at least one of measurement of the number of viable cells or a viable cell rate in the medical product, analysis of cell surface antigens, analysis of various expressed genes, analysis of the amount of various expressed genes, analysis of various cell functions, measurement of concentration of substances in a solvent, measurement of osmotic pressure, analysis of morphology and particle size of cell and distribution thereof, analysis of a color tone, measurement of a weight, detection and identification of pathogenic microorganisms included in the medical product, detection and identification of proliferating viruses, and the like. The production device 10 transmits the signal (final analysis data) indicating the analysis result of the medical product to the central management device 20.

Next, in the central management device 20, the initial analysis data, the initial processing data, and the final analysis data received or generated in this sequence are stored in association with each other (S24). These newly stored data are used as data for machine learning in the central management device 20 (S25).

The sequence shown in FIG. 9 has the same advantages as the sequence shown in FIG. 6. In addition, the medical product produced by the sequence shown in FIG. 9 may be either "autologous product" or "allogeneic product". When the medical product is the "autologous product", the sequence shown in FIG. 9 has the above-described advantages.

Further, in the sequence shown in FIG. 9, the central management device 20 uses the newly obtained analysis data and processing data as the machine learning data. As a result, it possible to improve the accuracy of processing conditions determined by the central management device 20 in proportion to the number of analysis data and processing data stored in the central management device 20. As a result, it is possible to reduce the probability that the performance and quality of the human or animal cells or tissues which are the starting materials deviate during the production process.

(5) As to Modifications

A sequence of a system of one embodiment of the present invention is not limited to the sequences shown in any of FIGS. 6 to 9. For example, a sequence for performing all of the processes (S11 to S17 and S21 to 25) shown in FIGS. 6 to 9 is also included in the sequence of the system according to one embodiment of the present invention. Further, the processes (S16, S23, and S17) related to the analysis and processing of the intermediate product shown in FIG. 8 can be performed a plurality of times.

What is claimed is:

1. A system including a production device comprising:
an analyzer that determines a number of living cells or percentage of cells that are living in human or animal cell or tissue that is a starting material of a medical product and generates data on the basis of the analyzation;
a communicator that transmits the generated data to a central management device via a network constructed by either a wired connection or a wireless connection and receives initial processing data indicating a processing condition of the starting material optimized by the central management device based on the generated data within a range of a predetermined design space as the processing condition of the starting material; and
a processor that processes the starting material according to the initial processing data to produce the medical product,
wherein, the central management device comprises:
a central storage that records the generated data transmitted by the communicator; and
a central processor that optimizes the processing condition of the starting material based on the generated data.

2. The production device according to claim 1, wherein the analyzer generates intermediate analysis data of the intermediate product obtained by processing the starting material,
the communicator transmits the intermediate analysis data to the central management device and receives intermediate processing data indicating the processing condition of the intermediate product optimized by the central management device based on the intermediate analysis data within a range of a predetermined design space as the processing condition of the intermediate product, and
the processor processes the intermediate product according to the intermediate processing data.

3. The production device according to claim 1, the analyzer measures at least one of the number of the viable cells and the viable cell rate.

4. The production device according to claim 1, wherein the processor cultivates the cell or tissue.

5. The production device according to claim 1, further comprising: a transfer unit that transfers the starting material from one of the analyzer and the processor to the other of the analyzer and the processor.

6. The production device according to claim 1, wherein the medical product is an autologous product.

7. The production device according to claim 1, wherein the analyzer generates final analysis data of the medical product produced from the starting material, and the communicator transmits the final analysis data to the central management device to record the final analysis data by associating the final analysis data with the generated data and the initial processing data in the central management device.

8. The plurality of production devices according to claim 7, wherein the central management device includes:
a central storage that records the generated data, the initial processing data, and the final analysis data transmitted from each of the plurality of production devices in association with each other;
a central analyzer that when a target production device transmits latest generated data newly generated in the target production device which is any one of the plurality of production devices, generates latest initial processing data optimal for the latest generated data by referring to the generated data, the initial processing data, and the final analysis data recorded in association with each other in the central storage; and
a central communicator that transmits the latest generated data to the target production device.

9. The system according to claim 1, wherein the communicator directly transmits the generated data to the central management device.

10. The system according to claim 1, and wherein the analyzer, the communicator, and the processor are local to a collection site of the starting material and the central management device is remote to the collection site of the starting material.

11. A system including a production device comprising:
an analyzer that determines a number of living cells or percentage of cells that are living in human or animal cell or tissue that is a starting material of a medical product and generates data on the basis of the analyzation and a clinical data of the human or animal;

a communicator that transmits the generated data to a central management device via a network constructed by either a wired connection or a wireless connection and receives initial processing data indicating a processing condition of the starting material optimized by the central management device based on the generated data within a range of a predetermined design space as the processing condition of the starting material; and a processor that processes the starting material according to the initial processing data to produce the medical product, wherein, the central management device comprises:
- a central storage that records the generated data transmitted by the communicator; and
- a central processor that optimizes the processing condition of the starting material based on the generated data.

12. A method for producing a medical product in a system including a production device, the production device is controlled by a central management device, the method comprising:

analyzing, by the production device, a number of living cells or percentage of cells that are living in human or animal cell or tissue that is a starting material of a medical product, and generating data on the basis of the analyzation;

transmitting, by the production device, the generated data to the central management device via a network constructed by either a wired connection or a wireless connection;

generating, by the central management device, initial processing data indicating a processing condition of the starting material optimized based on the generated data within a range of a predetermined design space as a processing condition of the starting material;

transmitting, by the central management device, the initial processing data to the production device; and processing, by the production device, the starting material according to the initial processing data to produce the medical product.

* * * * *